United States Patent [19]
Garnier et al.

[11] Patent Number: 6,087,519
[45] Date of Patent: Jul. 11, 2000

[54] RUBBER-TO-METAL ADHESION PROMOTER, METAL REINFORCEMENT, COMPOSITION MADE OF RUBBER, METAL REINFORCEMENT AND RUBBER-TO-METAL ADHESION PROMOTER, AND USE OF THE RUBBER-TO-METAL ADHESION PROMOTER

[75] Inventors: Francis Garnier, Champigny; Philippe Lang, Vincennes, both of France; Richard Michalitsch, Kopfstetten, Austria; Bernd Kaiser, Hannover, Germany; Gerhard E. Nauer, Vienna, Austria

[73] Assignee: Continental Aktiengesellschaft, Hannover, Germany

[21] Appl. No.: 08/834,415

[22] Filed: Apr. 16, 1997

[30] Foreign Application Priority Data

Apr. 17, 1996 [DE] Germany ............................ 196 15 134

[51] Int. Cl.$^7$ .................................. C07F 7/04; C07F 7/10
[52] U.S. Cl. ............................. 556/419; 556/438; 556/440; 556/465; 556/488; 556/489; 560/450; 560/495
[58] Field of Search ...................................... 556/419, 438, 556/440, 465, 488, 489; 560/450, 495

[56] References Cited

U.S. PATENT DOCUMENTS

| | | | |
|---|---|---|---|
| 3,896,175 | 7/1975 | Helmlinger et al. | 568/69 |
| 4,581,297 | 4/1986 | Delseth et al. | 428/462 |
| 5,113,004 | 5/1992 | Yanagisawa et al. | 556/440 |
| 5,126,385 | 6/1992 | Seibert et al. | 524/100 |
| 5,217,807 | 6/1993 | Steiber et al. | 428/378 |
| 5,466,848 | 11/1995 | Childress | 556/427 |
| 5,489,701 | 2/1996 | Childress et al. | 556/427 |
| 5,652,290 | 7/1997 | Nakamura et al. | 524/437 |

FOREIGN PATENT DOCUMENTS

| | | |
|---|---|---|
| 150168 | 7/1985 | European Pat. Off. . |
| 386905 | 9/1990 | European Pat. Off. . |
| 536545 | 4/1993 | European Pat. Off. . |
| 2221626 | 12/1972 | Germany . |
| 1177766 | 1/1970 | United Kingdom . |
| 9008170 | 7/1990 | WIPO . |

OTHER PUBLICATIONS

Patent Abstracts of Japan, vol. 18, No. 528 (C–1258), Oct. 6, 1994.

(List continued on next page.)

*Primary Examiner*—D. S. Nakarani
*Attorney, Agent, or Firm*—Greenblum & Bernstein, P.L.C.

[57] ABSTRACT

The invention relates to an adhesive substance for improved adhesion between a vulcanizable polymer and a metallic reinforcing carrier.

The use of an adhesive substance with the following structure is proposed in order to produce an improved adhesion between rubber and a metallic reinforcing carrier:

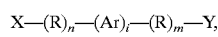

$$X-(R)_n-(Ar)_i-(R)_m-Y,$$

wherein

X: —SH; —Si(Cl)$_3$; —Si(OR$_1$)$_3$; —COOH
  with R$_1$: alkyl remainder (branched and unbranched), particularly —CH$_3$; —C$_2$H$_5$ or —C$_3$H$_7$;

R: —CH$_2$—; —CF$_2$—; wherein $0 \leq n,m \leq 12$, or —CH$_2$—CO—NH—CH$_2$—; —CF$_2$—CO—NH—CF$_2$—; —CH$_2$—CO—NH—CF$_2$—; —CF$_2$—CO—NH—CH$_2$—, wherein $0 \leq n,m \leq 4$ Ar: aromatic and/or heteroaromatic system, comprised of one or several of the following molecules:
  benzene, phenylene, aniline, thiophene, pyrrole, furane, with or without substituents
  wherein $0 \leq i \leq 6$, and Y: is an unsaturated hydrocarbon remainder, in particular a styrene, isoprene, vinyl, or acryl group.

16 Claims, 2 Drawing Sheets

OTHER PUBLICATIONS

Patent Abstracts of Japan, vol. 15, No. 48 (C–802), Feb. 5, 1991.

Patent Abstracts of Japan, vol. 10, No. 214 (C–362), Jul. 25, 1986.

Derwent's WPI Database, section CH, week 9614, class A18, AN 96–136353.

Derwent's WPI Database, section Ch, week 9431, class A13, AN 94–252856.

Derwent's WPI Database, section CH, week 9346, class A14, AN 93–365479.

Derwent's WPI Database, section CH, week 9106, class A85, AN 91–039593.

Derwent's WPI Database, section CH, week 9444, class A14, AN 94–354929.

RUBBER-TO-METAL ADHESION PROMOTER, METAL REINFORCEMENT, COMPOSITION MADE OF RUBBER, METAL REINFORCEMENT AND RUBBER-TO-METAL ADHESION PROMOTER, AND USE OF THE RUBBER-TO-METAL ADHESION PROMOTER

CROSS-REFERENCE OF RELATED APPLICATION

The present invention claims the priority under 35 U.S.C. § 119 of German Patent Application No. 196 15 134.1 filed on Apr. 17, 1996, the disclosure of which is expressly incorporated by reference herein in its entirety.

BACKGROUND OF THE INVENTION

1. Field of the Invention

The invention relates to an adhesive substance for improved adhesion between a vulcanizable polymer and a metallic reinforcing carrier.

2. Background and Material Information

In order to produce a sufficient and long-lasting adhesion of rubber to metal, many parameters have to be taken into consideration. The surface of the metallic reinforcing carrier has to be modified so that the rubber is permitted to adhere. To that end, up till this point, metallic reinforcing carriers (generally steel cord), which were to be imbedded in rubber mixtures that could be vulcanized with sulfur, were coated with a layer of brass. Further developments were made in which the brass was replaced by zinc-cobalt or zinc-nickel alloys (EP 536 545). The brass layer or zinc alloy is used to produce a mechanical denticulation with the rubber layer during the vulcanization through the formation of an intermediary layer. However, there is a disadvantage in that the intermediary layer does not cover the metallic reinforcing carrier (steel cord) in all places so that these places represent weak points in the adhesion. Furthermore, additional sulfur is required for the production of the intermediary layer and must also be added to the rubber mixture. In order to produce a permanent adhesion between rubber and metal, it is furthermore necessary for the rubber mixture to be very resistant to aging. That is why mixtures containing cobalt salts were proposed. These rubber mixtures, though, had the disadvantage of low durability.

For rubber coatings of steel cord, it is furthermore known that the addition of resorcinol-formaldehyde condensation products should increase the aging resistance of the rubber mixture. These condensation products, however, are toxicologic which makes processing them more difficult.

A variety of experiments have already been conducted in order to optimize the adhesion between rubber and metal. As a rule, though, it is still necessary to match the reinforcing carrier and the rubber mixture of the adhesive mixture to each other within strict limits. This in turn has the disadvantage that with the combination of another adjoining rubber layer, the composition of this must be adapted to that of the adhesive mixture and consequently can only be varied within strict limits. A variation of the rubber composition, though, has an effect on the properties of the rubber product so that they, too, cannot be optimally adjusted. The requirement for producing a long-lasting and stable adhesion to the steel cord thus limits the freedom to optimize other desirable mixture properties.

SUMMARY OF THE INVENTION

An object of the invention is to produce an improved adhesion between rubber and metallic reinforcing carriers which can be favorably achieved for technical process reasons.

This object is attained according to the invention by virtue of the fact that the adhesive substance has the following structure:

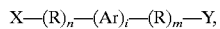

$$X\text{—}(R)_n\text{—}(Ar)_i\text{—}(R)_m\text{—}Y,$$

wherein

X: —SH; —Si(Cl)$_3$; —Si(OR$_1$)$_3$; —COOH
  with R$_1$: alkyl remainder (branched and unbranched), particularly —CH$_3$ —C$_2$H$_5$ or —C$_3$H$_7$;
R: —CH$_2$—; —CF$_2$—; wherein $0 \leq n,m \leq 12$, or
  —CH$_2$—CO—NH—CH$_2$—; —CF$_2$—CO—NH—CF$_2$—; —CH$_2$—CO—NH—CF$_2$—; —CF$_2$—CO—NH—CH$_2$—, wherein $0 \leq n,m \leq 4$
Ar: aromatic and/or heteroaromatic system, comprised of one or several of the following molecules:
  benzene, phenylene, aniline, thiophene, pyrrole, furane, with or without substituents
  wherein $0 \leq i \leq 6$, and
Y: is an unsaturated hydrocarbon remainder, in particular a styrene, isoprene, vinyl, or acryl group.

The invention is based on the knowledge that due to the functionality X, the above-mentioned classes of compounds have a high degree of adsorption force with regard to metallic surfaces and at the same time, due to the functionality Y, a covalent bond to the rubber is produced during its vulcanization. The use of these bifunctional classes of compounds as adhesives permits a strong adhesion of the rubber to the metallic reinforcing carrier.

Due to the above-mentioned X functionalities, adsorption produces a strong bond to the metallic or metal oxide surface. Conventional pure metals such as aluminum, in particular also the elements of the subgroups of the periodic system (e.g. platinum, titanium, silver, copper, nickel, zinc, iron), alloys such as steel and brass, as well as metal oxides such as aluminum oxide and iron oxide can be used for the metallic substrates. Due to the strong adsorption force of the X functionality in relation to the metallic surface, it is possible to deposit a monomolecular coating of adhesive substance on the metallic surface. Therefore only a small amount of adhesive substance is required, which is cost effective. It has turned out to be particularly advantageous that for the purpose of adhesion to the metallic substrate, the adhesive substance has a thiol group (—SH) as X, which in the optimum case has a covalent bond to the metal surface. It has been discovered that especially with these compounds, an adsorption in relation to the metallic surface occurs that is to a large extent spontaneous, which produces a monomolecular coating of the metallic surface.

As a further structural component of the class of compounds according to the invention, R (alkyl remainder, fluorinated alkyl remainder, alkyl remainder or fluorinated alkyl remainder with or without an acid amide grouping between them) functions as a "spacer". Depending on the size of n and m, the chain length of R can be varied. As a result, the mechanical stability (chain mobility) of the bond is influenced so that an optimal adaptation to the type of metallic surface or, by means of varying m, an optimal adaptation to the vulcanizable polymer can be produced.

As the aromatic and/or heteroaromatic systems, conventional compounds from the literature can be used, for example oligophenyls and oligothiophenes. There can be 0 to 6 aromatic units. Preferably substituents are disposed in this aromatic and/or heteroaromatic system, which are considerably electron repellent, such as an NH$_2$ grouping, an OCH grouping, or also are electron attracting substituents such as a CN grouping or an $NO_2$ grouping. Depending on the type of substituent, these can in turn exert an influence on the bonding to the metallic surface or to the vulcanizable polymer.

An aromatic and/or heteroaromatic system (Ar) that contains a thiophene component has also turned out to be favorable. As already mentioned in general for the aromatic and/or heteroaromatic system, the thiophene component of the adhesive substance can likewise be provided with suitable substituents. The thiophene ring can be bonded directly to R. However, it is also possible to bond the thiophene ring, with or without suitable substituents, to an already existing aromatic system. The process of electrodeposition has proven to be advantageous as a "bonding process" for bonding the thiophene, in particular, to an already existing aromatic system. In this electrochemical process, it is assumed that electrons are stripped from the thiophene through the influence of an electrical current. When a hydrogen proton splits off, the thiophene radical produced is in a position to bond to the already existing aromatic system. Since the voltage which is necessary for stripping an electron from the thiophene is relatively low, the thiophene is particularly suited for bonding to an already existing aromatic system by means of electrodeposition (grafting). In principle, though, other systems and also for example other monomeric or oligomeric components can also be bonded by means of this process.

As already mentioned, the adhesive substance according to the invention has a functionality Y, which permits it to form a covalent bond with the vulcanizable polymer. Y can be an unsaturated remainder such as $—CH=CH_2$; a styrene, isoprene, vinyl, or acryl group.

Depending on the type of polymer to be vulcanized, the functionality Y can be selected so that during the vulcanization, a permanent bond is produced between the polymer and the adhesive substance and consequently also in relation to the reinforcing carrier. Both elastomers and thermoplastic elastomers can be used as vulcanizable polymers. For example, natural rubber, styrene-butadiene rubber, butadiene rubber, butyl rubber, acrylonitrile butadiene rubber, ethylene propylene diene copolymer, or ethylene propylene copolymer can be used as elastomers. Polymers known from the prior art can be used as the thermoplastic elastomer. The depositing of the adhesive according to the invention onto the metallic reinforcing carrier permits an excellent bond at least between the elastomer block of the thermoplastic elastomer and the adhesive via its functionality Y. In this manner, a sufficient adhesion between the thermoplastic elastomer and the reinforcing carrier is already produced.

It is possible to activate the vulcanization by means of sulfur or by means of peroxides. In particular in sulfur vulcanization, the functionality Y of the adhesive substance must have double or triple bonds in order to be able to form a bond with the polymer.

For producing a composite of the metallic reinforcing carrier, the adhesive substance, and the vulcanizable polymer, it is advantageous if the adhesive substance is dissolved in an organic solvent and the metallic reinforcing carrier is drawn through this solution (dipping process). The adhesive substance can already have all the functionalities (X, Y) which are necessary for adhesion to both the reinforcing carrier and the vulcanizable polymer. The metallic reinforcing carriers coated with the adhesive substance can then be coated with a vulcanizable polymer and the vulcanization can be subsequently carried out. It is also possible, though, to add an adhesive substance to the dip solution, which substance does not yet have the complete structure of the adhesive substance according to the invention so that the metallic reinforcing carrier is first covered at least with the functionality (X) of the adhesive substance given to it. Next, for example by means of electrodeposition, the remaining structural part of the adhesive substance can then be bonded with the functionality (Y) to the part of the adhesive substance already adhering to the metallic reinforcing carrier. After this, as already mentioned, the vulcanizable polymer can be deposited and vulcanized.

In principle, though, still other options are also possible for conventionally depositing the adhesive substance onto the metallic reinforcing carrier, for example the conversion of the adhesive substance into a gaseous phase and the subsequent condensation of the substance on the metallic reinforcing carrier.

The use of the adhesive substance according to the invention, wherein as a rule, a monomolecular coating of the adhesive substance on the metallic reinforcing carrier is sufficient, achieves the fact that only a little of this substance is needed in order to coat the reinforcing carrier completely so that through the use of the adhesive substance according to the invention, a more reasonably priced production of a metal reinforced rubber product is possible. Through the variation of the components R and Ar as well as n and m, it is possible to act on the functionalities X and Y so that a variation of the bond strengths of the adhesive substance in relation to the metallic reinforcing carrier or to the vulcanizable polymer is assured. Therefore various types of metallic reinforcing carriers can be coated with different vulcanizable polymers, which have an excellent adhesion in relation to one another.

In principle, though, not even a monomolecular coating of the adhesive substance on the metallic reinforcing carrier is required (e.g. with thermoplastic elastomers). Adsorption forces or covalent bonds produce a permanent bond by means of the functionalities X and Y. The bond strength of a covalent bond is much greater than with a mechanical denticulation that produces the adhesion in conventional brass coatings, so that according to the invention, a more permanent adhesion is produced.

Furthermore, the disadvantage of the mechanical denticulation, namely an inadequate aging resistance of the bond, is prevented through the use of the adhesive substance according to the invention. Rubber products that are reinforced with metallic reinforcing carriers can now be produced according to the invention, which are corrosion resistant and have better mechanical properties. In polymers that can be vulcanized using sulfur, now it is no longer necessary to introduce a supplemental addition of sulfur into the rubber mixture, which was previously required for the formation of a sufficient adhesive layer for brass coated reinforcing carriers. Through the use of the adhesive substance according to the invention, a separate adhesive mixture can in fact be eliminated.

The adhesive substance according to the invention can be used for all rubber products that are reinforced with metallic reinforcing carriers, for example for conveyor belts, pneumatic springs, belts, hoses, and in particular, for vehicle tires. With the latter, in which the bead (generally solid rubber tires and pneumatic tires) and/or the belt layers and/or the casing are comprised of steel, particular advantages have been achieved through the use of the adhesive substance.

By omitting the adhesive mixtures, the individual rubber mixtures can be optimally matched to one another in the production of the vehicle tire so that it is now also possible according to the invention, for example, to deposit the tread mixture directly onto the belt. Consequently, the tire can be produced for a more reasonable price and at the same time, can be optimized in its running properties. Furthermore, the tire has a longer service life.

BRIEF DESCRIPTION OF THE DRAWINGS

An exemplary embodiment is explained in detail below in conjunction with the drawings.

cord is polarized as a working electrode belonging to this three-electrode cell. Another electrode is used as a reference (silver/silver nitrate electrode) and a platinum plate or another resistant anode material is used as a counter electrode. The voltage is increased from 0 to 0.75 V in 500 mV per second steps. Through the voltage applied, an electron is stripped from the thiophene and the remaining thiophene radical is in a position, through the abstraction of a hydrogen atom, to attach to the first component of the adhesive substance, which is already disposed on the reinforcing carrier (steel cord), wherein the mechanism of the attachment has not yet been explained.

The steps 1 and 4 are summarized again below

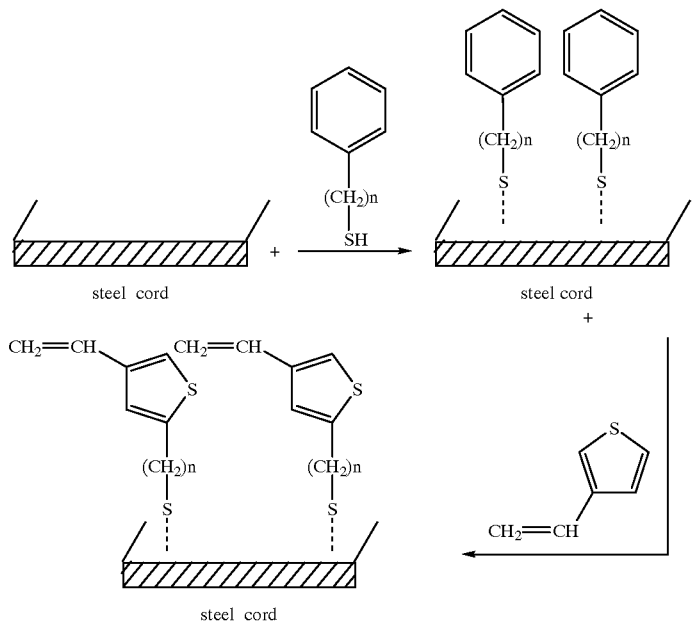

DETAILED DESCRIPTION OF THE PREFERRED EMBODIMENT

Figure 1:
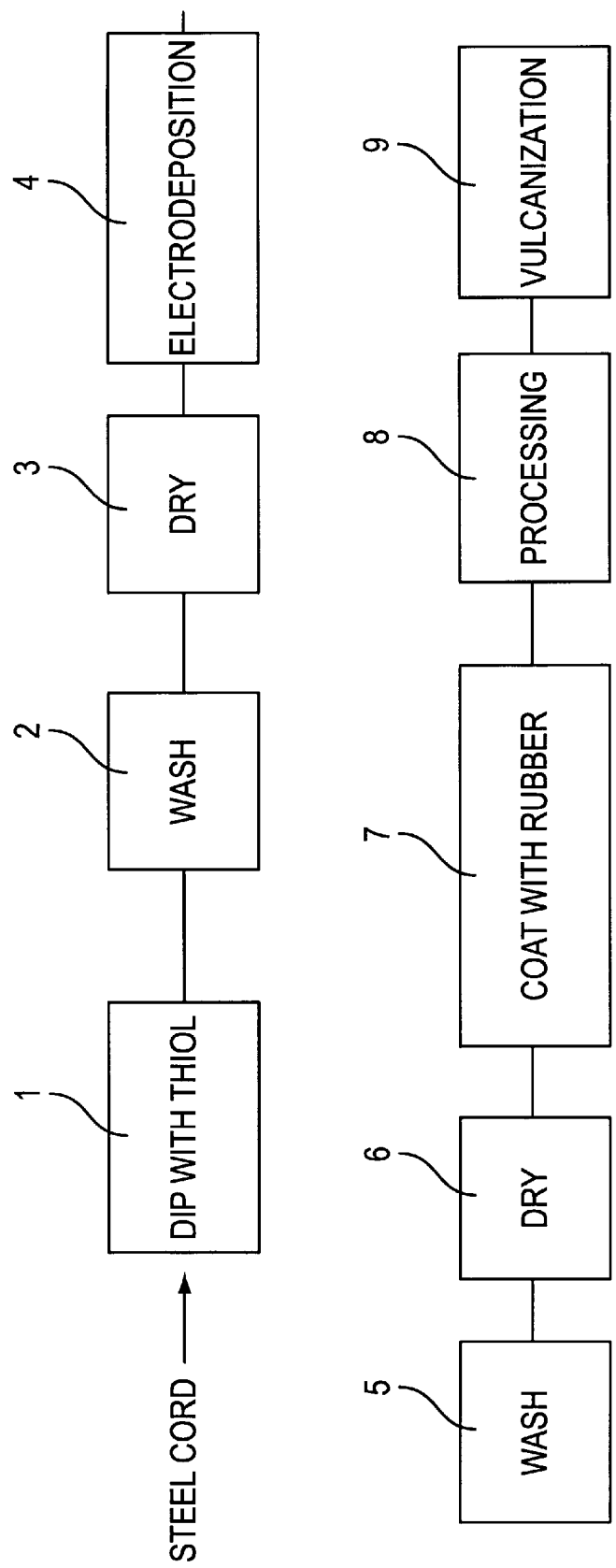
FIG. 1 shows the schematic course of the manufacture of a vulcanized composite of steel cord and a rubber mixture in which the substance according to the invention is used as an adhesive.

FIG. 1 schematically depicts the fact that a cord of an arbitrary type of steel (e.g. 0.8% carbon, trace elements) is treated in step 1 with a solution—in the simplest instance, thiophenol (phenyl methane thiol, phenyl ethane thiol, etc.) in toluene. In principle, alkylsilicon chloride, e.g. trichloromethylsilane, or alkylsiloxane, e.g. hexamethyldisiloxane, or organic acids (or organic acid chlorides) are used in lieu of a thiol. The concentration of the thiol in the solvent toluene is e.g. 0.1 molar. In step 2, excess thiol is rinsed from the steel cord with e.g. an alcoholic solution and in step 3, a drying process is carried out at approx. 60° C. Now a component of the adhesive substance according to the invention is disposed on the steel cord, which adhesive substance adheres to the metal (steel cord) by means of a covalent sulfur bond. By means of electrodeposition (step 4), now the part of the adhesive substance (Y) is bonded to the previously disposed component of the adhesive substance on the reinforcing carrier. To that end, the treated steel cord is guided into a three electrode cell in which the thiophene (e.g. vinyl thiophene in acetonitrile) is disposed as a 0.1 molar bath solution, wherein the steel the electrodeposition (step 4) is followed by a further washing process (step 5), for example with water, and then a drying process (step 6) takes place at approx. 60° C. The steps 4 to 6 can also be omitted if a sufficiently reactive adhesive substance can already be deposited on the steel cord with the dipping process (step 1). To this end, the X and Y functionality must already be present in the adhesive substance. The following compounds come into consideration as examples:

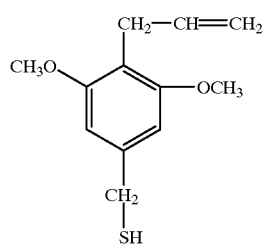

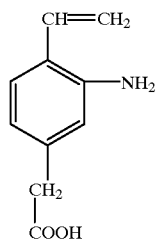

The coating of the steel cord with the adhesive substance is followed by step 7, namely the depositing of the unvulcanized rubber layer. The steel cord coated with adhesive is introduced into a calender and is covered with a calendered rubber plate (e.g. natural rubber mixture). This composite of steel cord, adhesive substance, and rubber plate can be processed further in a subsequent processing step 8 for the respective product manufacture. For the production of a pneumatic vehicle tire, for example, the composite could represent the belt packet, which is placed on the casing layer during construction of the tire. In the further production of the tire, the unvulcanized treads are deposited on the belt packet. After the completion of the tire blank, it is placed in the vulcanization press and is vulcanized at an increased pressure and temperature.

Figure 2:
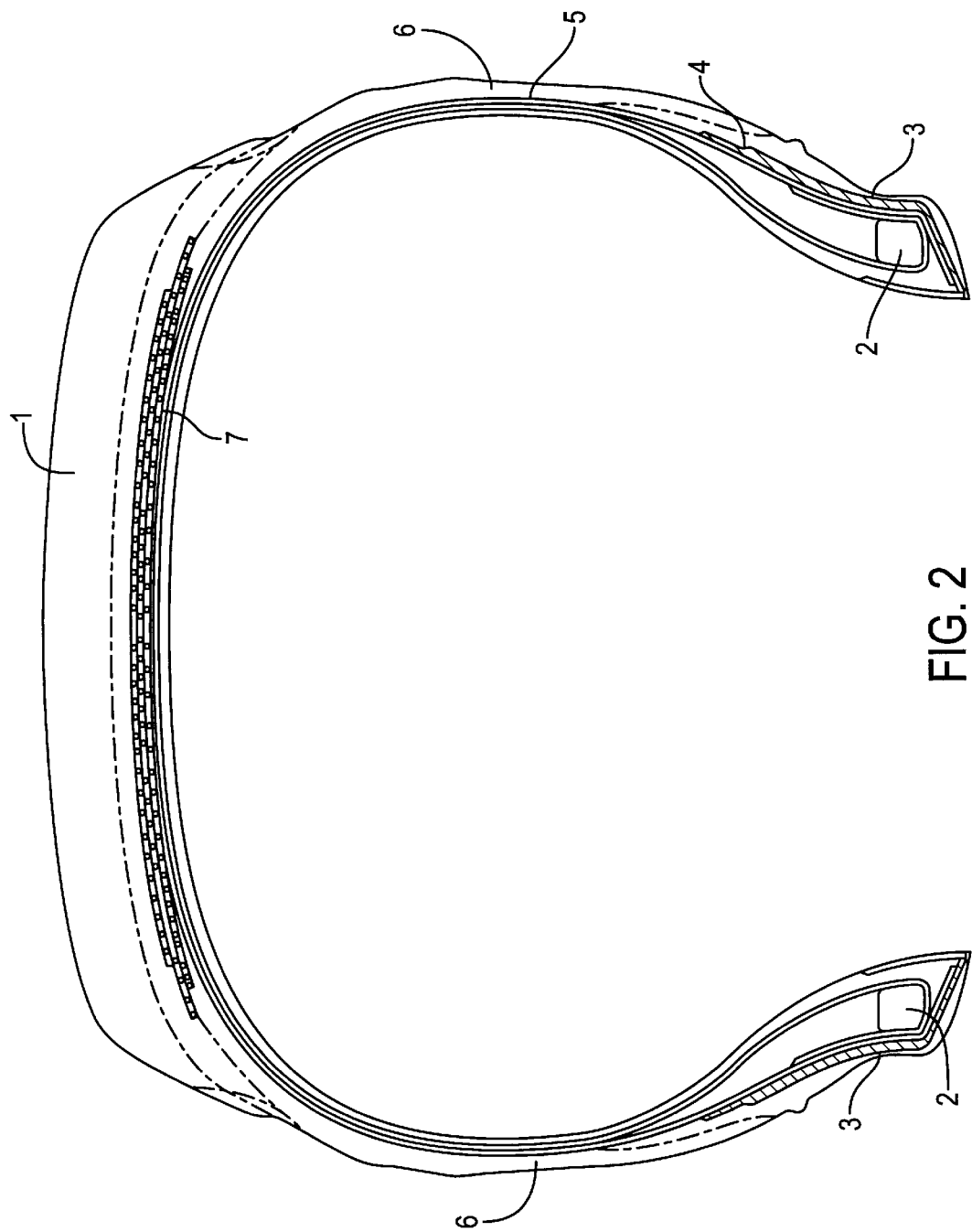
FIG. 2 shows a radial cross section through a pneumatic vehicle tire.

FIG. 2 depicts a pneumatic vehicle tire with a tread 1, metallic bead 2 disposed in the bead region 3, a bead reinforcer 4, a casing 5, side walls 6, and a metallic belt 7. In general, the bead 2 and the belt 7 are comprised of metallic reinforcing carriers. However, the casing 5 can also be comprised of steel cord. In particular, this kind of tires are for use in heavy commercial vehicles. Through the use of the adhesive substance according to the invention, tires can be produced at a more reasonable price since an additional adhesive mixture for metallic reinforcing carriers can be eliminated. Furthermore, the individual rubber mixtures can be better matched to one another so that the running properties of the tire can be optimized. Due to the favorable adhesion between the metallic reinforcing carrier and rubber, corrosion problems are to a large degree prevented so that the tire withstands greater mechanical loads and consequently has a longer service life.

What is claimed is:

1. An adhesive substance for improved adhesion between a vulcanizable polymer and a metallic reinforcing carrier, wherein the adhesive substance comprises a compound of the following structure:

$$X-(R)_n-(Ar)_i-(R)_m-Y,$$

wherein

X: is —SH; —Si(Cl)$_3$, —Si(OR$_1$)$_3$, —SiR$_2$(Cl)$_2$, —COOH,
wherein R$_1$ is —C$_3$H$_7$ and R$_2$ is a branched or straight chain alkyl group;

R: is —CH$_2$—, —CF$_2$—, wherein $0 \leq n, m \leq 12$; or —CH$_2$—CO—NH—CH$_2$—, —CF$_2$—CO—NH—CF$_2$—, —CH$_2$—CO—NH—CF$_2$—, —CF$_2$—CO—NH—CH$_2$—, wherein $0 \leq n, m \leq 4$;

Ar: is an aromatic and/or heteroaromatic system, comprising at least one member selected from the group consisting of:
substituted or unsubstituted benzene, phenylene, aniline, thiophene, pyrrole, and furane,
wherein $1 \leq i \leq 6$, and Y: is an unsaturated hydrocarbon group.

2. The adhesive substance according to claim 1, wherein X is an —SH group.

3. The adhesive substance according to claim 1, wherein at least one part of the aromatic and/or heteroaromatic system (Ar) is bonded to the compound by electrodeposition of monomeric or oligomeric components.

4. The adhesive substance according to claim 1, wherein the substituent of the aromatic and/or heteroaromatic system (Ar) acts as an electron donor or acceptor.

5. The adhesive substance according to claim 1, wherein Y comprises at least one member selected from the group consisting of styrene, isoprene, vinyl, and acryl.

6. The adhesive substance according to claim 5, wherein Y comprises styrene.

7. The adhesive substance according to claim 5, wherein Y comprises isoprene.

8. The adhesive substance according to claim 5, wherein Y comprises vinyl.

9. The adhesive substance according to claim 5, wherein Y comprises acryl.

10. An adhesive substance for improved adhesion between a vulcanizable polymer and a metallic reinforcing carrier, wherein the adhesive substance comprises a compound of the following structure:

$$X-(R)_n-(Ar)_i-(R)_m-Y,$$

wherein

X: is —Si(OR$_1$)$_3$
wherein R$_1$ is C$_2$H$_5$;

R: is —CH$_2$—, —CF$_2$—, wherein $0 \leq n, m \leq 12$; or —CH$_2$—CO—NH—CH$_2$—, —CF$_2$—CO—NH—CF$_2$—, —CH$_2$—CO—NH—CF$_2$—, —CF$_2$—CO—NH—CH$_2$—, wherein $0 \leq n, m \leq 4$;

Ar: is a heteroaromatic system, comprising at least one member selected from the group consisting of:
substituted or unsubstituted aniline, thiophene, pyrrole, and furane,
wherein $1 \leq i \leq 6$, and Y: is an unsaturated hydrocarbon group.

11. The adhesive substance according to claim 10, wherein at least one part of the aromatic and/or heteroaromatic system (Ar) is bonded to the compound by electrodeposition of monomeric or oligomeric components.

12. The adhesive substance according to claim 10, wherein the substituent of the aromatic and/or heteroaromatic system (Ar) acts as an electron donor or acceptor.

13. The adhesive substance according to claim 10, wherein R$_1$ comprises a member selected from the group consisting of —CH$_3$ and —C$_2$H$_5$.

14. The adhesive substance according to claim 10, wherein Y comprises at least one member selected from the group consisting of styrene and isoprene.

15. The adhesive substance according to claim 14, wherein Y comprises styrene.

16. The adhesive substance according to claim 14, wherein Y comprises isoprene.

* * * * *